United States Patent
Atiya et al.

(10) Patent No.: US 10,260,869 B2
(45) Date of Patent: *Apr. 16, 2019

(54) CHROMATIC CONFOCAL SYSTEM

(71) Applicant: ALIGN TECHNOLOGY, INC., San Jose, CA (US)

(72) Inventors: Yossef Atiya, Maccabim (IL); Tal Verker, Ofra (IL)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/668,197

(22) Filed: Aug. 3, 2017

(65) Prior Publication Data

US 2017/0328704 A1    Nov. 16, 2017

Related U.S. Application Data

(63) Continuation of application No. 14/980,337, filed on Dec. 28, 2015, now Pat. No. 9,752,867, which is a
(Continued)

(51) Int. Cl.
*G01B 11/25* (2006.01)
*A61C 9/00* (2006.01)
(Continued)

(52) U.S. Cl.
CPC .......... *G01B 11/25* (2013.01); *A61B 1/00009* (2013.01); *A61B 1/04* (2013.01);
(Continued)

(58) Field of Classification Search
CPC ............ G01B 11/24; G01B 11/25; A61B 1/06
(Continued)

(56) References Cited

U.S. PATENT DOCUMENTS 2,467,432 A  4/1949 Kesling
3,407,500 A  10/1968 Kesling
(Continued)

FOREIGN PATENT DOCUMENTS

AU    3031677 A    5/1979
AU    517102 B2    7/1981
(Continued)

OTHER PUBLICATIONS

AADR. American Association for Dental Research, Summary of Activities, Mar. 20-23, 1980, Los Angeles, CA, p. 195.
(Continued)

*Primary Examiner* — Roy M Punnoose
(74) *Attorney, Agent, or Firm* — Wilson Sonsini Goodrich & Rosati

(57) ABSTRACT

A system for determining surface topography of a three-dimensional structure is provided. The system can include an illumination unit configured to output a two-dimensional array of light beams each comprising a plurality of wavelengths. An optical assembly can focus the plurality of wavelengths of each light beam to a plurality of focal lengths so as to simultaneously illuminate the structure over a two-dimensional field of view. A detector and a processor are used to generate data representative of the surface topography of the three-dimensional structure based on the measured characteristics of the light reflected from the structure.

24 Claims, 8 Drawing Sheets

Related U.S. Application Data continuation of application No. 14/323,225, filed on Jul. 3, 2014, now Pat. No. 9,261,358.

(51) Int. Cl.
*G01B 11/24* (2006.01)
*A61C 1/08* (2006.01)
*A61B 1/00* (2006.01)
*A61B 1/04* (2006.01)
*A61B 1/06* (2006.01)
*A61B 1/24* (2006.01)
*A61B 5/107* (2006.01)
*A61B 5/00* (2006.01)

(52) U.S. Cl.
CPC .............. *A61B 1/06* (2013.01); *A61B 1/0638* (2013.01); *A61B 1/24* (2013.01); *A61B 5/0088* (2013.01); *A61B 5/1076* (2013.01); *A61B 5/1079* (2013.01); *A61B 5/4547* (2013.01); *A61C 1/088* (2013.01); *A61C 9/006* (2013.01); *A61C 9/0066* (2013.01); *G01B 11/24* (2013.01); *G01B 2210/50* (2013.01)

(58) Field of Classification Search
USPC ........................................................ 356/601
See application file for complete search history.

(56) References Cited

U.S. PATENT DOCUMENTS

| | | |
|---|---|---|
| 3,600,808 A | 8/1971 | Reeve |
| 3,660,900 A | 5/1972 | Andrews |
| 3,676,671 A * | 7/1972 | Sheldon ................ H01J 31/28 250/227.2 |
| 3,683,502 A | 8/1972 | Wallshein |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,368,955 A | 1/1983 | Masson |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A * | 3/1986 | Moermann ........ A61C 13/0004 700/163 |
| 4,588,265 A | 5/1986 | Takahashi |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A * | 5/1987 | Duret ...................... A61C 9/00 700/163 |
| 4,664,626 A | 5/1987 | Kesling |
| 4,676,747 A | 6/1987 | Kesling |
| 4,742,464 A * | 5/1988 | Duret ................ A61C 13/0004 700/183 |
| 4,755,139 A | 7/1988 | Abbatte et al. |
| 4,763,791 A | 8/1988 | Halverson et al. |
| 4,783,593 A | 11/1988 | Noble |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A * | 10/1990 | Steinbichler ........ A61C 13/0003 433/223 |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,132,143 A | 7/1992 | Deckard |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,239,178 A * | 8/1993 | Derndinger .............. G01B 9/04 250/234 |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,372,502 A | 12/1994 | Massen et al. |
| 5,378,154 A * | 1/1995 | Van Der Zel ...... A61C 13/0004 433/223 |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,503,152 A * | 4/1996 | Oakley .................... A61B 8/08 128/916 |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A * | 12/1996 | Andersson ......... A61C 13/0004 700/98 |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,659,420 A * | 8/1997 | Wakai .................. G01B 11/026 356/511 |
| 5,668,665 A | 9/1997 | Choate |
| 5,683,243 A | 11/1997 | Andreiko et al. |

(56) References Cited

U.S. PATENT DOCUMENTS

| | | | |
|---|---|---|---|
| 5,692,894 A | 12/1997 | Schwartz et al. | |
| 5,725,376 A | 3/1998 | Poirier | |
| 5,725,378 A | 3/1998 | Wang | |
| 5,733,126 A | 3/1998 | Andersson et al. | |
| 5,737,084 A * | 4/1998 | Ishihara | G01B 11/026 356/609 |
| 5,740,267 A | 4/1998 | Echerer et al. | |
| 5,742,700 A | 4/1998 | Yoon et al. | |
| 5,790,242 A | 8/1998 | Stern et al. | |
| 5,799,100 A | 8/1998 | Clarke et al. | |
| 5,800,174 A | 9/1998 | Andersson | |
| 5,823,778 A | 10/1998 | Schmitt et al. | |
| 5,848,115 A | 12/1998 | Little et al. | |
| 5,857,853 A | 1/1999 | Van Nifterick et al. | |
| 5,866,058 A | 2/1999 | Batchelder et al. | |
| 5,879,158 A | 3/1999 | Doyle et al. | |
| 5,880,961 A | 3/1999 | Crump | |
| 5,880,962 A | 3/1999 | Andersson et al. | |
| 5,934,288 A | 8/1999 | Avila et al. | |
| 5,957,686 A | 9/1999 | Anthony | |
| 5,964,587 A | 10/1999 | Sato | |
| 5,971,754 A | 10/1999 | Sondhi et al. | |
| 5,975,893 A | 11/1999 | Chishti et al. | |
| 6,015,289 A | 1/2000 | Andreiko et al. | |
| 6,044,309 A | 3/2000 | Honda | |
| 6,049,743 A | 4/2000 | Baba | |
| 6,062,861 A | 5/2000 | Andersson | |
| 6,068,482 A | 5/2000 | Snow | |
| 6,099,314 A | 8/2000 | Kopelman et al. | |
| 6,123,544 A | 9/2000 | Cleary | |
| 6,152,731 A | 11/2000 | Jordan et al. | |
| 6,183,248 B1 | 2/2001 | Chishti et al. | |
| 6,190,165 B1 | 2/2001 | Andreiko et al. | |
| 6,217,325 B1 | 4/2001 | Chishti et al. | |
| 6,217,334 B1 | 4/2001 | Hultgren | |
| 6,236,521 B1 | 5/2001 | Nanba | |
| 6,244,861 B1 | 6/2001 | Andreiko et al. | |
| 6,263,234 B1 * | 7/2001 | Engelhardt | A61B 5/0088 600/476 |
| 6,309,215 B1 | 10/2001 | Phan et al. | |
| 6,315,553 B1 | 11/2001 | Sachdeva et al. | |
| 6,322,359 B1 | 11/2001 | Jordan et al. | |
| 6,350,120 B1 | 2/2002 | Sachdeva et al. | |
| 6,382,975 B1 | 5/2002 | Poirier | |
| 6,398,548 B1 | 6/2002 | Muhammad et al. | |
| 6,399,942 B1 * | 6/2002 | Ishihara | G02B 21/004 250/234 |
| 6,402,707 B1 | 6/2002 | Ernst | |
| 6,482,298 B1 | 11/2002 | Bhatnagar | |
| 6,524,101 B1 | 2/2003 | Phan et al. | |
| 6,554,611 B2 | 4/2003 | Chishti et al. | |
| 6,572,372 B1 | 6/2003 | Phan et al. | |
| 6,573,998 B2 | 6/2003 | Cohen-Sabban | |
| 6,594,539 B1 | 7/2003 | Geng | |
| 6,629,840 B2 | 10/2003 | Chishti et al. | |
| 6,697,164 B1 | 2/2004 | Babayoff et al. | |
| 6,705,863 B2 | 3/2004 | Phan et al. | |
| 6,722,880 B2 | 4/2004 | Chishti et al. | |
| 6,940,611 B2 | 9/2005 | Babayoff et al. | |
| 7,092,107 B2 | 8/2006 | Babayoff et al. | |
| 7,230,725 B2 | 6/2007 | Babayoff et al. | |
| 7,319,529 B2 | 1/2008 | Babayoff | |
| 7,446,885 B2 * | 11/2008 | Zabolitzky | G01B 9/04 356/601 |
| 7,477,402 B2 | 1/2009 | Babayoff et al. | |
| 7,511,829 B2 | 3/2009 | Babayoff | |
| 7,561,273 B2 | 7/2009 | Stautmeister et al. | |
| 7,626,705 B2 | 12/2009 | Altendorf | |
| 7,630,089 B2 | 12/2009 | Babayoff et al. | |
| 7,672,527 B2 | 3/2010 | Arenberg et al. | |
| 7,724,378 B2 | 5/2010 | Babayoff | |
| 7,791,810 B2 | 9/2010 | Powell | |
| 7,796,277 B2 | 9/2010 | Babayoff et al. | |
| 7,944,569 B2 | 5/2011 | Babayoff et al. | |
| 7,990,548 B2 | 8/2011 | Babayoff et al. | |
| 8,126,025 B2 | 2/2012 | Takeda | |
| 8,310,683 B2 | 11/2012 | Babayoff et al. | |
| 8,451,456 B2 | 5/2013 | Babayoff | |
| 8,488,113 B2 | 7/2013 | Thiel et al. | |
| 8,577,212 B2 | 11/2013 | Thiel | |
| 8,638,447 B2 | 1/2014 | Babayoff et al. | |
| 8,638,448 B2 | 1/2014 | Babayoff et al. | |
| 8,675,706 B2 | 3/2014 | Seurin et al. | |
| 8,743,923 B2 | 6/2014 | Geske et al. | |
| 8,767,270 B2 | 7/2014 | Curry et al. | |
| 9,089,277 B2 | 7/2015 | Babayoff et al. | |
| 9,261,356 B2 * | 2/2016 | Lampert | G01B 11/24 |
| 9,261,358 B2 | 2/2016 | Atiya et al. | |
| 9,393,087 B2 | 7/2016 | Moalem | |
| 9,439,568 B2 | 9/2016 | Atiya et al. | |
| 9,675,429 B2 * | 6/2017 | Lampert | G01B 11/24 |
| 9,696,264 B2 * | 7/2017 | Lange | G01N 21/9501 |
| 9,752,867 B2 * | 9/2017 | Atiya | G01B 11/25 |
| 9,844,427 B2 | 12/2017 | Atiya et al. | |
| 9,939,258 B2 * | 4/2018 | Lampert | G01B 11/24 |
| 2002/0006597 A1 | 1/2002 | Andreiko et al. | |
| 2002/0023903 A1 | 2/2002 | Ann Ngoi et al. | |
| 2002/0030812 A1 | 3/2002 | Ortyn et al. | |
| 2003/0009252 A1 | 1/2003 | Pavlovskaia et al. | |
| 2003/0139834 A1 | 7/2003 | Nikolskiy et al. | |
| 2003/0224311 A1 | 12/2003 | Cronauer | |
| 2004/0128010 A1 | 7/2004 | Pavlovskaia et al. | |
| 2005/0055118 A1 | 3/2005 | Nikolskiy et al. | |
| 2005/0283065 A1 | 12/2005 | Babayoff | |
| 2006/0158665 A1 | 7/2006 | Babayoff et al. | |
| 2007/0109559 A1 | 5/2007 | Babayoff et al. | |
| 2007/0114362 A1 | 5/2007 | Feng et al. | |
| 2007/0211605 A1 | 9/2007 | Sakamoto | |
| 2009/0051995 A1 | 2/2009 | Shechterman | |
| 2009/0218514 A1 | 9/2009 | Klunder et al. | |
| 2009/0219612 A1 | 9/2009 | Hirata | |
| 2010/0099984 A1 | 4/2010 | Graser et al. | |
| 2011/0080576 A1 | 4/2011 | Thiel et al. | |
| 2012/0081786 A1 | 4/2012 | Mizuyama et al. | |
| 2012/0147912 A1 | 6/2012 | Moench et al. | |
| 2012/0281293 A1 | 11/2012 | Gronenborn et al. | |
| 2013/0163627 A1 | 6/2013 | Seurin et al. | |
| 2013/0177866 A1 | 7/2013 | Babayoff et al. | |
| 2013/0266326 A1 | 10/2013 | Joseph et al. | |
| 2013/0286174 A1 | 10/2013 | Urakabe | |
| 2014/0022356 A1 | 1/2014 | Fisker et al. | |
| 2014/0104620 A1 | 4/2014 | Babayoff et al. | |
| 2014/0139634 A1 | 5/2014 | Lampert et al. | |
| 2015/0037750 A1 | 2/2015 | Moalem | |
| 2016/0000535 A1 | 1/2016 | Atiya et al. | |
| 2016/0003610 A1 | 1/2016 | Lampert et al. | |
| 2016/0003613 A1 | 1/2016 | Atiya et al. | |
| 2016/0015489 A1 | 1/2016 | Atiya et al. | |
| 2016/0064898 A1 | 3/2016 | Atiya et al. | |
| 2016/0109226 A1 | 4/2016 | Atiya et al. | |
| 2017/0027670 A1 | 2/2017 | Atiya et al. | |
| 2018/0235738 A1 | 8/2018 | Atiya et al. | |

FOREIGN PATENT DOCUMENTS

| | | |
|---|---|---|
| AU | 5598894 A | 6/1994 |
| CA | 1121955 A | 4/1982 |
| CN | 1646894 A | 7/2005 |
| DE | 2749802 A1 | 5/1978 |
| DE | 69327661 T2 | 7/2000 |
| DE | 102005043627 A1 | 3/2007 |
| DE | 102012009836 A1 | 11/2013 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| EP | 1970668 A1 | 9/2008 |
| EP | 1970743 A1 | 9/2008 |
| EP | 2213223 A1 | 8/2010 |
| EP | 2439489 A2 | 4/2012 |

(56) References Cited

FOREIGN PATENT DOCUMENTS

| | | |
|---|---|---|
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-9924786 A1 | 5/1999 |
| WO | WO-0008415 A1 | 2/2000 |
| WO | WO-02095475 A1 | 11/2002 |
| WO | WO-2007090865 A1 | 8/2007 |
| WO | WO-2012083967 A1 | 6/2012 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.
Alexander et al., "The DigiGraph Work Station Part 2 Clinical Management," JCO, pp. 402-407 (Jul. 1990).
Altschuler, "3D Mapping of Maxillo-Facial Prosthesis," AADR Abstract #607, 2 pages total, (1980).
Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue a, p. 221.
Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space-Coded by a Laser-Projected Dot Matrix," SPIE Imaging Applications for Automated Industrial Inspection and Assembly, vol. 182, p. 187-191 (1979).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "Integrated Three-Dimensional Craniofacial Mapping: Background, Principles, and Perspectives," Semin. in Orthod., 7(4):223-232 (Dec. 2001).
Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff, "Computerized Diagnostic Setups and Simulations," Angle Orthod., 40(1):28-36 (Jan. 1970).
Biggerstaff et al., "Computerized Analysis of Occlusion in the Postcanine Dentition," Am. J. Orthod., 61(3): 245-254 (Mar. 1972).
Biostar Operation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004.
Bourke, "Coordinate System Transformation," (Jun. 1996), p. 1, retrieved from the Internet Nov. 5, 2004, URL< http://astronomy.swin.edu.au/—pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form in Predetermination, Am, Journal of Orthodontics, vol. 79, No. 2 (Feb. 1981), pp. 115-133.
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Cardinal Industrial Finishes, Powder Coatings information posted at<http://www.cardinalpaint.com>on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
CEREC Omnicam and CEREC Bluecam brochure. The first choice in every case. The Dental Company Sirona. 2014.
Chaconas et al., "The DigiGraph Work Station, Part 1, Basic Concepts," JCO, pp. 360-367 (Jun. 1990).
Chafetz et al., "Subsidence of the Femoral Prosthesis, a Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision,"Part 3 the Computer Gives New Vision—Literally," Part 4 Bytes 'N Bites—The Computer Moves from the Front Desk to the Operatory, Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et al., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.

(56) References Cited

OTHER PUBLICATIONS

Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
Dummer, et al. Computed Radiography Imaging Based on High-Density 670 nm VCSEL Arrays. Proceedings of SPIE vol. 7557, 75570H (2010)http://vixarinc.com/pdf/SPIE_radiography_manuscript_submission1.pdf.
DuraClear™ product information, Allesee Orthodontic Appliances-Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet<http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamara, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).

Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page 1998).
International search report and written opinion dated Oct. 23, 2015 for PCT/IB2015/054911.
"International search report with written opinion dated Oct. 15, 2015 for PCT/IB2015/054910".
Jco Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
Mccann, "Inside the ADA," J. Amer. Dent. Assoc., 118:286-294 (Mar. 1989).
Mcnamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).

(56) References Cited

OTHER PUBLICATIONS

Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. Of the IEEE Industrial Electronics Society (IECON '98), Sep. 4, 1998, pp. 2415-2418.
Pellin Broca Prisms—Specifications. Thor Labs. Updated Nov. 30, 2012. www.thorlabs.com.
Pinkham, "Foolish Concept Propels Technology," Dentist, 3 pages total, Jan./Feb. 1989.
Pinkham, "Inventors CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances,< http:// www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, a Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).

Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the minipositioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients,<http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20,1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment

(56) References Cited

OTHER PUBLICATIONS

Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be a Candidate for This Invisible No-Braces Treatment, Allesee Orthodontic Appliances—Pro Lab product information for patients, 2 pages (2002).
Ishii. Fast Focus Mechanism Using a Pair of Convergent and Divergent Lenses Differentially for Three-dimensional Imaging. IEICE Transactions on Information and Systems. Jan. 1, 2012. pp. 168-172.
Schaack. Variation of Magnification with Focus. Applied Optics, vol. 41, No. 7. Mar. 1, 2002. p. 1282.

\* cited by examiner

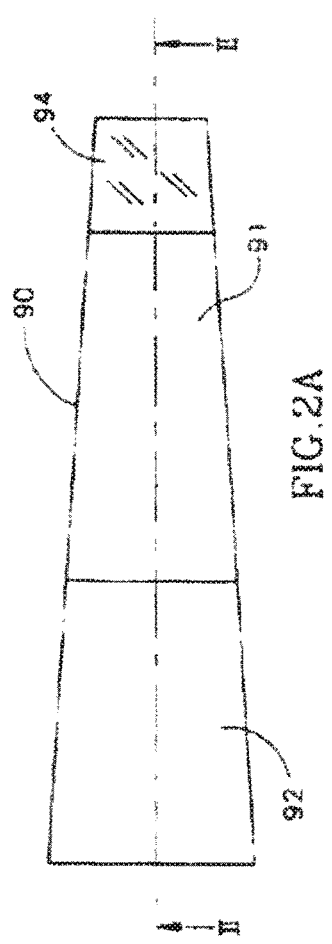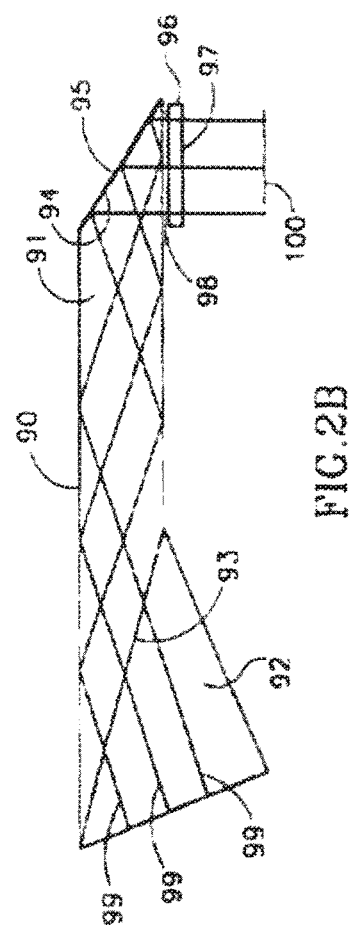
FIG. 2A
FIG. 2B

CHROMATIC CONFOCAL SYSTEM

CROSS-REFERENCE

This application is a continuation application of U.S. application Ser. No. 14/980,337, filed Dec. 28, 2015, now U.S. Pat. No. 9,752,867, issued Sep. 5, 2017, which is a is a continuation application of U.S. application Ser. No. 14/323,225, filed Jul. 3, 2014, now U.S. Pat. No. 9,261,358, issued Feb. 16, 2016, each of which is incorporated herein by reference in their entirety.

BACKGROUND

A variety of approaches have been developed for measuring surface topography optically. For example, optical systems and methods have been developed and employed that can be used to optically measure surface topography of a patient's teeth. The measured surface topography of the teeth can be used, for example, to design and manufacture a dental prosthesis and/or to determine an orthodontic treatment plan to correct a malocclusion.

One technique for measuring surface topography optically employs laser triangulation to measure distance between a surface of the tooth and an optical distance probe, which is inserted into the oral cavity of the patient. Surface topography measured via laser triangulation, however, may be less accurate than desired due to, for example, suboptimal reflectivity from the surface of the tooth.

Other techniques for measuring surface topography optically, which are embodied in CEREC-1 and CEREC-2 systems commercially available from Siemens GmbH or Sirona Dental Systems, utilize the light-section method and phase-shift method, respectively. Both systems employ a specially designed hand-held probe to measure the three-dimensional coordinates of a prepared tooth. Both of these approaches, however, require a specific coating (i.e. measurement powder and white-pigments suspension, respectively) to be deposited to the tooth. The thickness of the coating layer should meet specific, difficult to control requirements, which leads to inaccuracies in the measurement data.

In yet another technique, mapping of teeth surface is based on physical scanning of the surface by a probe and by determining the probe's position, e.g., by optical or other remote sensing means.

U.S. Pat. No. 5,372,502 discloses an optical probe for three-dimensional surveying. Various patterns are projected onto the tooth or teeth to be measured and corresponding plurality of distorted patterns are captured by the optical probe. Each captured pattern provides refinement of the topography.

SUMMARY

Systems and methods for optically determining surface topography of three-dimensional structures are provided. In many embodiments, a system for optically determining surface topography includes an optical assembly configured to focus a two-dimensional array of light beams each comprising a plurality of wavelengths to a plurality of focal lengths relative to the optical assembly. The systems and methods described herein provide chromatic confocal scanning of three-dimensional structures without using an axial scanning mechanism (e.g., mechanism for scanning in the direction of propagation of the chief rays of the incident light), thus enabling smaller and faster scanning optics. The systems and methods described herein can also be used to provide chromatic confocal scanning of three-dimensional structures without using a lateral scanning mechanism, thereby further enabling smaller and faster scanning optics. Furthermore, embodiments described herein permit scanning using a two-dimensional array of light beams focused to a continuous spectrum of focal lengths, thereby providing improved measurement accuracy, resolution, and depth.

Thus, in one aspect, a system for determining surface topography of a three-dimensional structure is provided. The system can include an illumination unit, an optical assembly, a detector, and a processor. The illumination unit can be configured to output a two-dimensional array of light beams each comprising a plurality of wavelengths. The optical assembly can be configured to focus the plurality of wavelengths of each light beam of to a plurality of focal lengths relative to the optical assembly so as to simultaneously illuminate the structure over a two-dimensional field of view. The detector can be configured to measure a characteristic of light reflected from the structure for each of a plurality of locations distributed in two dimensions over the field of view. The processor can be operatively coupled with the detector and configured to generate data representative of the surface topography of the structure based on the measured characteristics of the light reflected from the structure.

In another aspect, a method for determining surface topography of a three-dimensional structure is provided. The method includes generating a two-dimensional array of light beams each comprising a plurality of wavelengths. The plurality of wavelengths of each light beam can be focused to a plurality of focal lengths relative to the structure so as to simultaneously illuminate the structure over a two-dimensional field of view. A characteristic of light reflected from the structure can be measured for each of a plurality of locations distributed in two dimensions over the field of view. Data representative of the surface topography of the structure can be generated based on the measured characteristics of the light reflected from the structure.

Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A is a top view of a probing member, in accordance with many embodiments;

FIG. 2B is a longitudinal cross-section through line II-II in FIG. 2A, depicting exemplary rays passing there through;

DETAILED DESCRIPTION

Figure 1A:
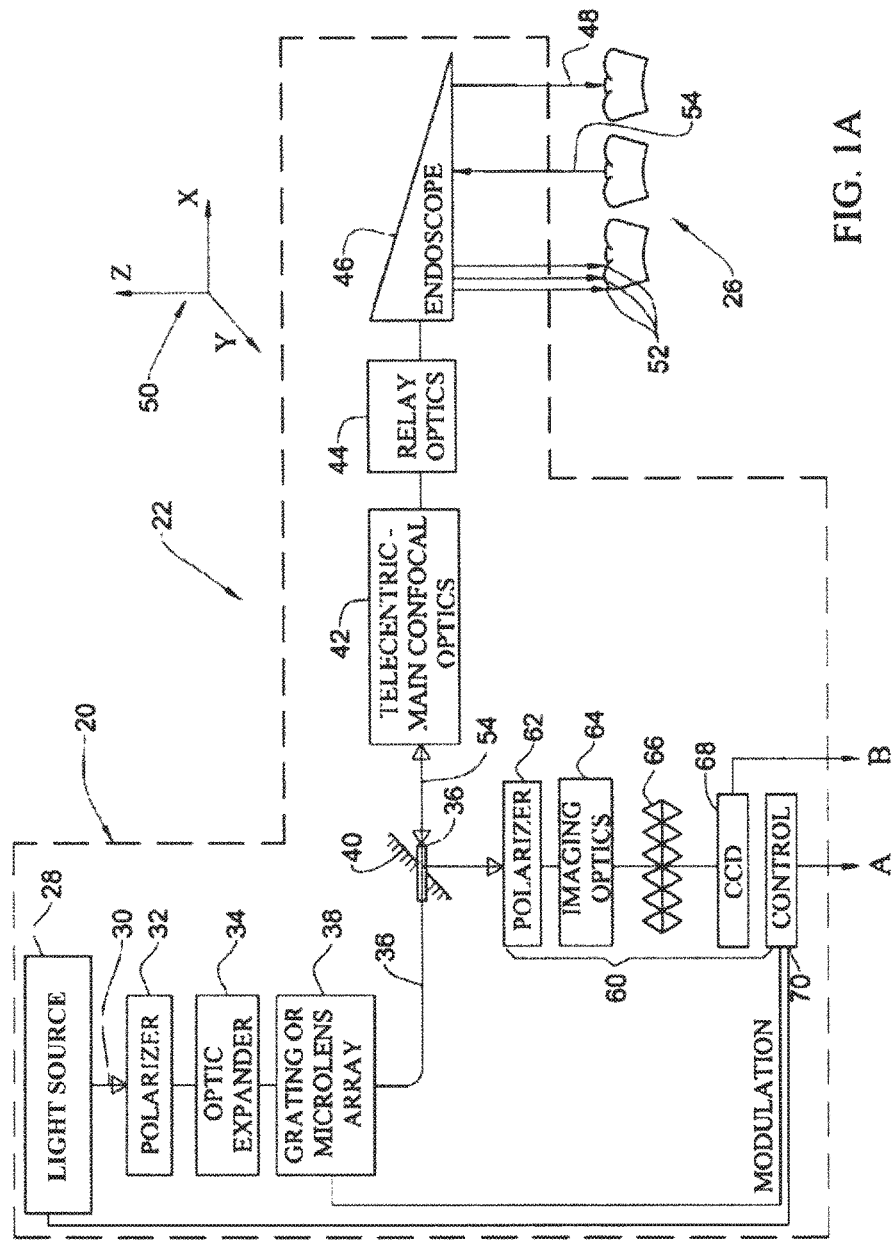
FIGS. 1A and 1B schematically illustrate, by way of a block diagram, an apparatus in accordance with many embodiments (FIG. 1B is a continuation of FIG. 1A)

In many embodiments, the systems and methods described herein for determining surface topography of a three-dimensional structure focus a two-dimensional array of light beams that each include a plurality of wavelengths to a plurality of focal lengths relative to an optical assembly. The surface topography can be ascertained by determining, at each point in a two-dimensional field of view, the wavelength having the best focus. Since each wavelength of the plurality of wavelengths is focused to a unique respective focal length, the distance to each point can thus be inferred. The structure being measured can be simultaneously illuminated with the array of light beams over the two-dimensional field of view. In many embodiments, the two-dimensional array of light beams projects a two-dimensional array of spots onto the structure. Light reflected from each of the spots on the structure over the two-dimensional field of view can be directed onto a two-dimensional detector configured to process the reflected light to determine, for each location of the reflected light distributed over the two-dimensional field of view, a characteristic of the light indicative of the respective distance to the structure being measured. In contrast to prior approaches that require a lateral scanning mechanism (a mechanism for scanning the light laterally relative to the direction of propagation of the chief rays of light used to illuminate the structure), the embodiments disclosed herein provide optical measurements without a lateral scanning mechanism. The use of a two-dimensional spot array for illuminating the structure may provide improved measurement depth, accuracy, and resolution compared to prior approaches. In many embodiments, the plurality of focal lengths covers a sufficient overall distance so that no axial scanning mechanism (a mechanism for scanning the plurality of focal lengths relative to the optical assembly) is required. In many embodiments, the wavelengths of the light beams are focused to a continuous spectrum of focal lengths, which may provide increased measurement accuracy compared to prior approaches. Accordingly, the optical systems described herein can be smaller, more compact, and faster than conventional systems.

The array of light beams can be used to simultaneously illuminate the structure over the two-dimensional field of view, thereby generating returning light reflected from the structure over the two-dimensional field of view. One or more characteristics of the returning reflected light can be measured for each point in the field of view and used to determine the distance to the structure for each of the points. Suitable characteristics can include intensity, wavelength, polarization, phase shift, interference, and/or dispersion of the returning light beams. Any description herein relating to light intensity can also be applied to other suitable characteristics of light, and vice-versa.

For example, in many embodiments, the intensity of a particular returning wavelength for a particular point in the two-dimensional field of view is maximized when the wavelength is focused on the surface of the structure. Accordingly, by focusing each light beam to the plurality of focal lengths relative to the optical assembly so as to illuminate the structure over the two-dimensional field of view, the relative distance to the structure from the optical assembly from which the light is emitted can be determined for each point in the field of view based on which returning wavelength has the highest measured intensity for the respective point in the field of view. In many embodiments, the plurality of focal lengths covers a sufficient depth so as to obviate the need for axial scanning of the wavelengths to identify the in-focus distance, thereby enabling completely static imaging optics. By decreasing the need for axial scanning, the cost, weight, and size of the optical measurement device can be reduced, and faster optical scans are possible.

The systems and methods described herein can be used to take optical measurements of the surfaces of any suitable three-dimensional structure. In many embodiments, optical measurements are taken to generate data representing the three-dimensional surface topography of a patient's dentition. The data can be used, for example, to produce a three-dimensional virtual model of the dentition that can be displayed and manipulated. The three-dimensional virtual models can be used to, for example, define spatial relationships of a patient's dentition that are used to create a dental prosthesis (e.g., a crown or a bridge) for the patient. The surface topography data can be stored and/or transmitted and/or output, such as to a manufacturing device that can be used to, for example, make a physical model of the patient's dentition for use by a dental technician to create a dental prosthesis for the patient.

In one aspect, a system for determining surface topography of a three-dimensional structure is provided. The system can comprise an illumination unit, an optical assembly, a detector, and a processor. The illumination unit is configured to output a two-dimensional array of light beams, each light beam comprising a plurality of wavelengths. The optical assembly can be operatively coupled to the illumination unit and configured to focus the plurality of wavelengths of each light beam to a plurality of focal lengths relative to the optical assembly so as to simultaneously illuminate the structure over a two-dimensional field of view. The detector can be configured to measure a characteristic of light reflected from the structure for each of a plurality of locations distributed in two dimensions over the field of view. The processor can be coupled with the detector and configured to generate data representative of the surface topography of the structure based on the measured characteristics of the light reflected from the structure. In many embodiments, the characteristic comprises an intensity.

Any suitable plurality of wavelengths can be used. In many embodiments, the two-dimensional array of light beams comprises broad-band light beams. The plurality of wavelengths can include wavelengths from 400 nm to 800 nm. The plurality of wavelengths can comprise at least three spectral bands, and the at least three spectral bands may comprise overlapping wavelengths of light. The plurality of wavelengths may comprise a continuous spectrum of wavelengths.

The two-dimensional array of light beams may form a two-dimensional array of spots on the structure over the field of view. A ratio of pitch to spot size for the two-dimensional array of spots can be configured to inhibit cross-talk between the two-dimensional array of spots.

In many embodiments, the optical assembly is configured to focus the light beams of the two-dimensional array to the plurality of focal lengths using at least one optical component with longitudinal chromatic aberration. The plurality of focal lengths may provide for a sufficient range of measurement depth without any axial scanning of the distance between the optical assembly and the focal lengths. For example, the plurality of focal lengths can cover a depth of at least 20 mm. In many embodiments, the plurality of focal lengths covers a depth of about 30 mm. In many embodiments, the plurality of focal lengths can be fixed relative to the optical assembly.

In many embodiments, the detector includes a plurality of sensor elements distributed over a surface area configured to receive the light reflected from the structure over the field of view. Each sensor element can be configured to measure the intensity of at least one wavelength of the light reflected from the structure. For example, the sensor elements can include a plurality of red sensor elements, a plurality of green sensor elements, and a plurality of blue sensor elements. Each of the red sensor elements is configured to measure the intensity of a red light wavelength. Each of the green sensor elements is configured to measure the intensity of a green light wavelength. And each of the blue sensor elements is configured to measure the intensity of a blue light wavelength. In many embodiments, the sensor elements can be arranged in a Bayer pattern. Alternatively, the sensor elements can be arranged in a modified Bayer pattern, or any other suitable pattern. Furthermore, in some instances, the sensor elements can be arranged in a plurality of layers.

In many embodiments, the optical assembly is configured to focus the plurality of wavelengths to the plurality of focal lengths without using an axial scanning mechanism. The optical assembly can be configured to focus the plurality of wavelengths to the plurality of focal lengths relative to the optical assembly without relative movement of components of the optical assembly and components of the illumination unit. The optical assembly can focus the plurality of wavelengths to the plurality of focal lengths to a depth within a range from 10 mm to 30 mm.

In another aspect, a method for determining surface topography of a three-dimensional structure is provided. The method can include generating a two-dimensional array of light beams each comprising a plurality of wavelengths. The plurality of wavelengths of each light beam can be focused to a plurality of focal lengths relative to the structure so as to simultaneously illuminate the structure over a two-dimensional field of view. A characteristic of the light reflected from the structure can be measured for each of a plurality of locations distributed in two dimensions over the field of view. Data representative of the surface topography of the structure can be generated based on the measured characteristics of the light reflected from the structure. In many embodiments, the measured characteristic comprises an intensity.

Any suitable plurality of wavelengths can be used. In many embodiments, the two-dimensional array of light beams comprises broad-band light beams. The plurality of wavelengths can include wavelengths from 400 nm to 800 nm. The plurality of wavelengths may comprise at least three spectral bands, and the at least three spectral bands may comprise overlapping wavelengths of light. The plurality of wavelengths may comprise a continuous spectrum of wavelengths.

The two-dimensional array of light beams may form a two-dimensional array of spots on the structure over the field of view. A ratio of pitch to spot size for the two-dimensional array of spots can be configured to inhibit cross-talk between the two-dimensional array of spots.

In many embodiments, the optical assembly is configured to focus the light beams of the two-dimensional array to the plurality of focal lengths using at least one optical component with longitudinal chromatic aberration. The plurality of focal lengths may provide for a sufficient range of measurement depth without any axial scanning of the distance between the optical assembly and the focal lengths. For example, the plurality of focal lengths can cover a depth of at least 20 mm. In many embodiments, the plurality of focal lengths covers a depth of about 30 mm. In many embodiments, the plurality of focal lengths can be fixed relative to the optical assembly.

In many embodiments, the detector includes a plurality of sensor elements distributed over a surface area configured to receive the light reflected from the structure over the field of view. Each sensor element can be configured to measure the intensity of at least one wavelength of the light reflected from the structure. For example, the sensor elements can include a plurality of red sensor elements, a plurality of green sensor elements, and a plurality of blue sensor elements. Each of the red sensor elements is configured to measure the intensity of a red light wavelength. Each of the green sensor elements is configured to measure the intensity of a green light wavelength. And each of the blue sensor elements is configured to measure the intensity of a blue light wavelength. In many embodiments, the sensor elements can be arranged in a Bayer pattern. Alternatively, the sensor elements can be arranged in a modified Bayer pattern, or any other suitable pattern. Furthermore, in some instances, the sensor elements can be arranged in a plurality of layers.

In many embodiments, the focusing of the plurality of wavelengths to the plurality of focal lengths is performed without using an axial scanning mechanism. The focusing of the plurality of wavelengths to the plurality of focal lengths can be formed without relative movement of components of an optical assembly and components of an illumination unit. The optical assembly can focus the plurality of wavelengths to the plurality of focal lengths to a depth within a range from 10 mm to 30 mm.

Figure 1B:
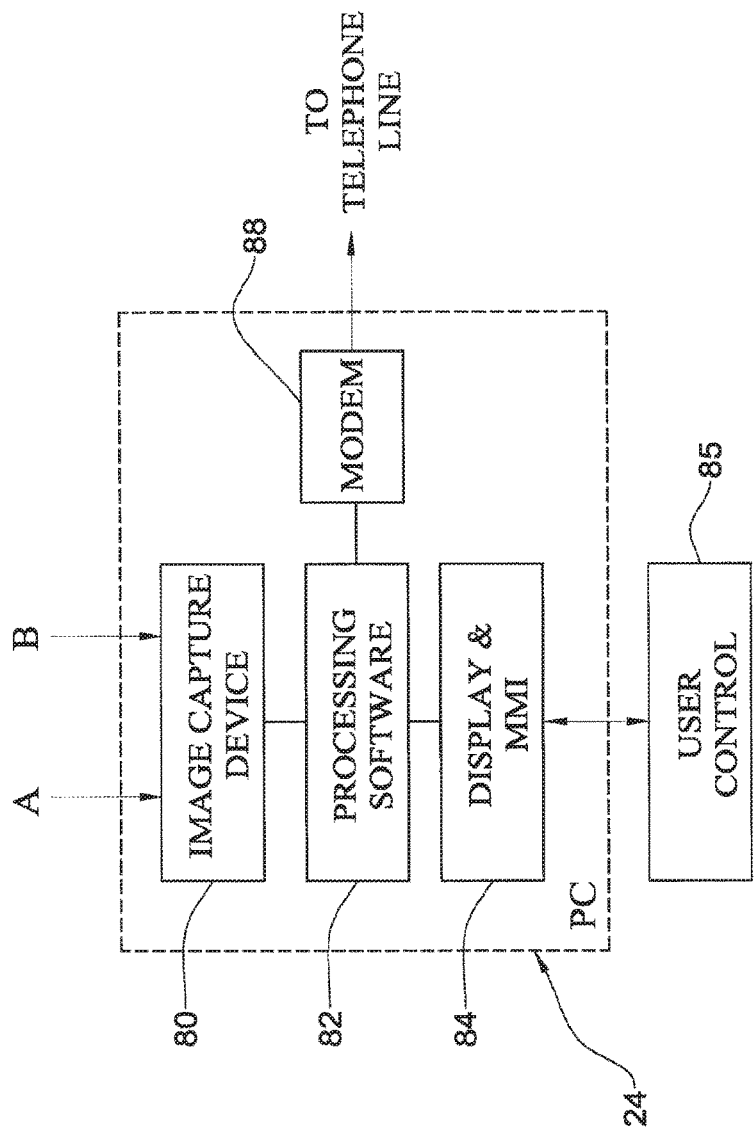

Turning now to the drawings, in which like numbers designate like elements in the various figures, FIGS. 1A and 1B illustrate an apparatus 20 for measuring surface topography optically. The apparatus 20 includes an optical device 22 coupled to a processor 24. The embodiment illustrated in FIG. 1 is particularly useful for measuring surface topography of a patient's teeth 26. For example, the apparatus 20 can be used to measure surface topography of a portion of the patient's teeth where at least one tooth or portion of tooth is missing to generate surface topography data for subsequent use in design and/or manufacture of a prosthesis for the patient (e.g., a crown or a bridge). It should be noted, however, that the invention is not limited to measuring surface topography of teeth, and applies, mutatis mutandis, also to a variety of other applications of imaging of three-dimensional structure of objects (e.g., for the recordal of archeological objects, for imaging of a three-dimensional structure of any suitable item such as a biological tissue, etc.).

The optical device 22 includes, in the illustrated embodiment, a light source 28 emitting light, as represented by arrow 30. In many embodiments, the light source is configured to emit light having a plurality of wavelengths, such as broad-band light. For example, the light source can be a broad-band light source, such as a white light source. The light passes through a polarizer 32, which causes the light passing through the polarizer 32 to have a certain polarization. The light then enters into an optic expander 34, which increases the diameter of the light beam 30. The light beam 30 then passes through a module 38, which can, for example, be a grating or a micro lens array that splits the parent beam 30 into a plurality of light beams 36, represented here, for ease of illustration, by a single line.

The optical device 22 further includes a partially transparent mirror 40 having a small central aperture. The mirror 40 allows transfer of light from the light source 28 through the downstream optics, but reflects light travelling in the opposite direction. It should be noted that in principle, rather than a partially transparent mirror, other optical components with a similar function may be used (e.g., a beam splitter). The aperture in the mirror 40 improves the measurement accuracy of the apparatus. As a result of this mirror structure, the light beams produce a light annulus with respect to a particular wavelength on the illuminated area of the imaged object as long as the area is not in focus relative to the particular wavelength. The annulus becomes a sharply-focused illuminated spot with respect to the particular wavelength when the particular wavelength is in focus relative to the imaged object. Accordingly, a difference between the measured intensity of the particular wavelength when out-of-focus and in-focus is larger. Another advantage of a mirror of this kind, as opposed to a beam splitter, is that internal reflections that occur in a beam splitter are avoided, and hence the signal-to-noise ratio is greater.

The optical device 22 further includes confocal optics 42, typically operating in a telecentric mode, relay optics 44, and an endoscopic probe member 46. In many embodiments, the confocal optics 42 is configured to avoid distance-introduced magnification changes and maintain the same magnification of the image over a wide range of distances in the Z direction (the Z direction being the direction of beam propagation). The confocal optics 42 optics can include an optical assembly configured to focus the light to a plurality of focal lengths along the Z direction, as described in further detail below. In many embodiments, the relay optics 44 is configured to maintain a certain numerical aperture of the light beam's propagation.

The endoscopic probe member 46 can include a light-transmitting medium, which can be a hollow object defining within it a light transmission path or an object made of a light transmitting material (e.g., a glass body or tube). The light-transmitting medium may be rigid or flexible (e.g., fiber optics). In many embodiments, the endoscopic probe member 46 includes a mirror of the kind ensuring total internal reflection and directing the incident light beams towards the patient's teeth 26. The endoscope 46 thus emits a plurality of incident light beams 48 impinging on to the surface of the patient's teeth 26.

The incident light beams 48 form an array of light beams arranged in an X-Y plane, relative to a Cartesian reference frame 50, and propagating along the Z-axis. In many embodiments, each of the incident light beams 48 includes a plurality of wavelengths focused to a plurality of focal lengths relative to the endoscopic probe member 46. When the incident light beams 48 are incident upon an uneven surface, resulting illuminated spots 52 are displaced from one another along the Z-axis, at different $(X_i, Y_i)$ locations. Thus, while a particular wavelength of an illuminated spot 52 at a one location may be in focus, the same wavelength of illuminated spots 52 at other locations may be out of focus. Additionally, while one wavelength of an illuminated spot 52 may be in focus, other wavelengths of the same illuminated spot 52 may be out of focus. Therefore, returned wavelengths corresponding to focused incident wavelengths will have the highest light intensities, while returned wavelengths corresponding to out-of-focus incident wavelengths will have lower light intensities. Thus, for each illuminated spot, measurement of light intensity can be made for each of a plurality of different wavelengths spanning different fixed focal lengths. The relative Z distance between the endoscope 46 and the respective illuminated spot 52 can be determined by identifying the focal length corresponding to the returned wavelength having the peak measured light intensity.

The light reflected from each of the illuminated spots 52 includes a beam travelling initially in the Z axis in the opposite direction of the optical path traveled by the incident light beams. Each returned light beam 54 corresponds to one of the incident light beams 36. Given the asymmetrical properties of mirror 40, the returned light beams 54 are reflected in the direction of a detection assembly 60. The detection assembly 60 includes a polarizer 62 that has a plane of preferred polarization oriented normal to the polarization plane of polarizer 32. The returned polarized light beam 54 pass through imaging optics 64, typically a lens or a plurality of lenses, and then through an array of pinholes 66. Each returned light beam 54 passes at least partially through a respective pinhole of the array of pinholes 66. A sensor array 68 (e.g., a charge-coupled device (CCD) sensor array) includes a matrix of sensing elements. In many embodiments, each sensing element represents a pixel of the image and each sensing element corresponds to one pinhole in the array 66. The sensor array 68 can be configured to detect the intensities of each of a plurality of wavelengths of the returned light beams 54, as described in further detail below.

The sensor array 68 is connected to an image-capturing module 80 of the processor unit 24. The light intensity measured by each of the sensing elements of the sensor array 68 is analyzed, in a manner described below, by the processor 24. Although the optical device 22 is depicted in FIGS. 1A and 1B as measuring light intensity, the device 22 can also be configured to measure other suitable characteristics (e.g., wavelength, polarization, phase shift, interference, dispersion), as previously described herein.

The optical device 22 includes a control module 70 that controls operation of the light source 28. The control module 70 synchronizes the operation of the image-capturing module 80 with the operation of the light source 28 during acquisition of data representative of the light intensity from each of the sensing elements.

The intensity data is processed by the processor 24 per processing software 82 to determine relative intensity in each pixel over the entire range of wavelengths of light (e.g., using a suitable color analysis algorithm). As explained above, when a wavelength of a light spot is in focus on the three-dimensional structure being measured, the measured intensity of the wavelength of the corresponding returning light beam will be maximal. Thus, by determining the wavelength corresponding to the maximal light intensity, for each pixel, the relative in-focus focal length along the Z-axis can be determined for each light beam. Thus, data representative of the three-dimensional topography of the external surfaces of the teeth is obtained. A resulting three-dimensional representation can be displayed on a display 84 and manipulated for viewing (e.g., viewing from different angles, zooming in or out) by a user control module 85 (e.g., utilizing a computer keyboard, mouse, joystick, or touchscreen). In addition, the data representative of the surface topography can be transmitted through an appropriate data port such as, for example, a modem 88 or any suitable communication network (e.g., a telephone network) to a recipient (e.g., to an off-site CAD/CAM apparatus).

By capturing, in this manner, relative distance data between the probe and the structure being measured from two or more angular locations around the structure (e.g., in the case of a teeth segment, from the buccal direction, lingual direction and/or optionally from above the teeth), an accurate three-dimensional representation of the structure can be generated. The three-dimensional data and/or the resulting three-dimensional representation can be used to create a virtual model of the three-dimensional structure in a computerized environment and/or a physical model fabricated in any suitable fashion (e.g., via a computer controlled milling machine, a rapid prototyping apparatus such as a stereolithography apparatus).

As already pointed out above, a particular and preferred application is imaging of a segment of teeth having at least one missing tooth or a portion of a tooth. The resulting three-dimensional surface topography data can, for example, be used for the design and subsequent manufacture of a crown or any other prosthesis to be fitted into this segment.

Referring now to FIGS. 2A and 2B, a probing member 90 is illustrated in accordance with many embodiments. The probing member 90 can be made of a light transmissive material, (e.g., glass, crystal, plastic, etc.) and includes a distal segment 91 and a proximal segment 92, tightly glued together in an optically transmissive manner at 93. A slanted face 94 is covered by a reflective mirror layer 95. A transparent disk 96 (e.g., made of glass, crystal, plastic, or any other suitable transparent material) defining a sensing surface 97 is disposed along the optical path distal to the mirror layer 95 so as to leave an air gap 98 between the transparent disk 96 and the distal segment 91. The transparent disk 96 is fixed in position by a holding structure (not shown). Three light rays 99 are represented schematically. As can be seen, the light rays 99 reflect from the walls of the probing member 90 at an angle in which the walls are totally reflective, reflect from the mirror layer 95, and then propagate through the sensing face 97. A first wavelength of the light rays 99 is focused on a focusing plane 100.

Figure 3:
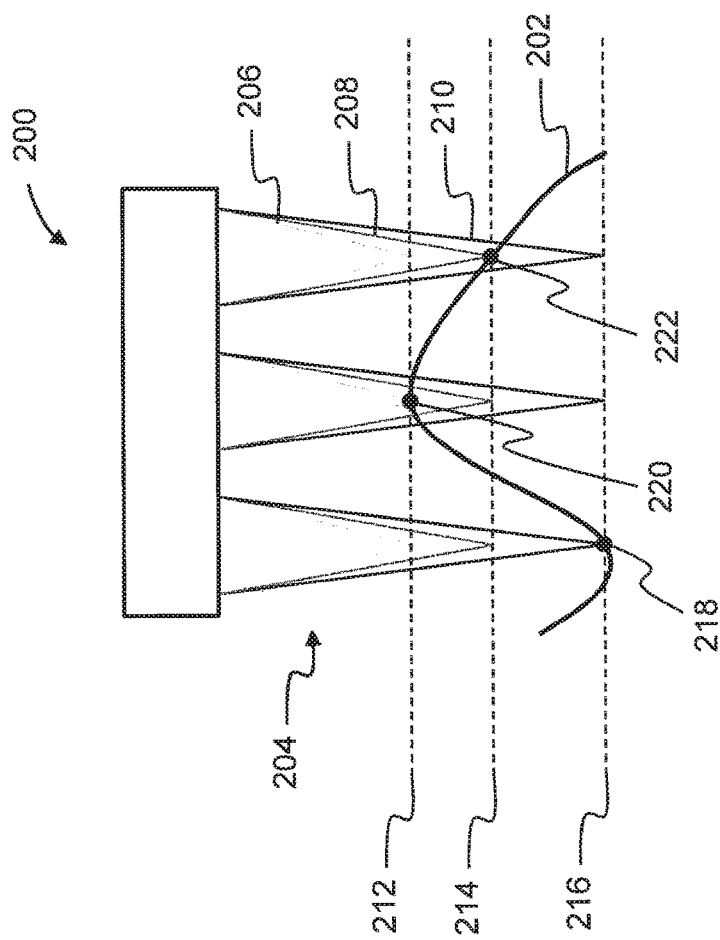
FIG. 3 illustrates an optical probe illuminating a three-dimensional structure, in accordance with many embodiments.

FIG. 3 illustrates an optical probe 200 illuminating a three-dimensional structure 202, in accordance with many embodiments. The probe 200 can illuminate the structure 202 over a two-dimensional field of view with a plurality of light beams 204 that are each focused to a plurality of focal lengths relative to the probe 200. The light beams 204 may each comprise a plurality of wavelengths. For example, the light beams 204 are each illustrated via representative wavelengths (a first wavelength 206, a second wavelength 208, and a third wavelength 210). The representative wavelengths may each have a respective fixed focal length relative to the probe 200 and are therefore focused to respective fixed focal lengths 212, 214, and 216. Accordingly, at spot 218 on the structure 202, the third wavelength 210 is in focus, while first and second wavelengths 206, 208 are out of focus. Similarly, at spot 220, the first wavelength 206 is in focus, while at spot 222, the second wavelength 208 is in focus. The relative distances between the optical probe 200 and the spots 218, 220, and 222 can thus be determined based on the fixed focal lengths of the third, first, and second wavelengths, respectively.

The optical probe 200 can be used in conjunction with any suitable device producing a plurality of wavelengths of light, such the embodiments described herein. For example, the light source 28 of the optical device 22 can be used to generate light that includes a plurality of wavelengths, including the wavelengths 206, 208, and 210. The light may be passed through a grating or microlens array 38 or other suitable optics in order to provide a two-dimensional array of light beams. The two-dimensional array of light beams can be projected onto the structure 202 so as to form a two-dimensional array of light spots, as described below.

The plurality of wavelengths for each light beam may include a plurality of discrete wavelengths, a continuous spectrum of wavelengths, or suitable combinations thereof. In many embodiments, the plurality of wavelengths may include wavelengths from 400 nm to 800 nm. The wavelengths may include at a plurality of spectral bands, such as at least three spectral bands. The spectral bands may include overlapping wavelengths of light. Alternatively or in combination, the spectral bands may include wavelengths of light that do not overlap with each other. For example, the wavelengths can include a red light wavelength (e.g., a wavelength between about 640 nm and about 660 nm), a green light wavelength (e.g., a wavelength between about 500 nm and about 520 nm), and a blue light wavelength (e.g., a wavelength between about 465 nm and about 485 nm). In many embodiments, the plurality of wavelengths may include a spectrum of wavelengths having a continuous distribution, such as a wavelength distribution spanning at least a portion of the visible spectrum. The plurality of wavelengths of light can be focused relative to the optical probe 200 to a plurality of focal lengths covering a suitable depth or range of depths, such as a depth of at least approximately 5 mm, 10 mm, 20 mm, 30 mm, 40 mm, 50 mm, or more. The depth can be within a range between any two of the following: 5 mm, 10 mm, 20 mm, 30 mm, 40 mm, or 50 mm. In many embodiments, the wavelengths are focused along a continuous range of fixed focal lengths, such that the focal lengths differ by an infinitesimal amount. The wavelengths can be focused to the corresponding focal lengths without requiring the movement of any optical components, as described in greater detail below.

Figure 4:
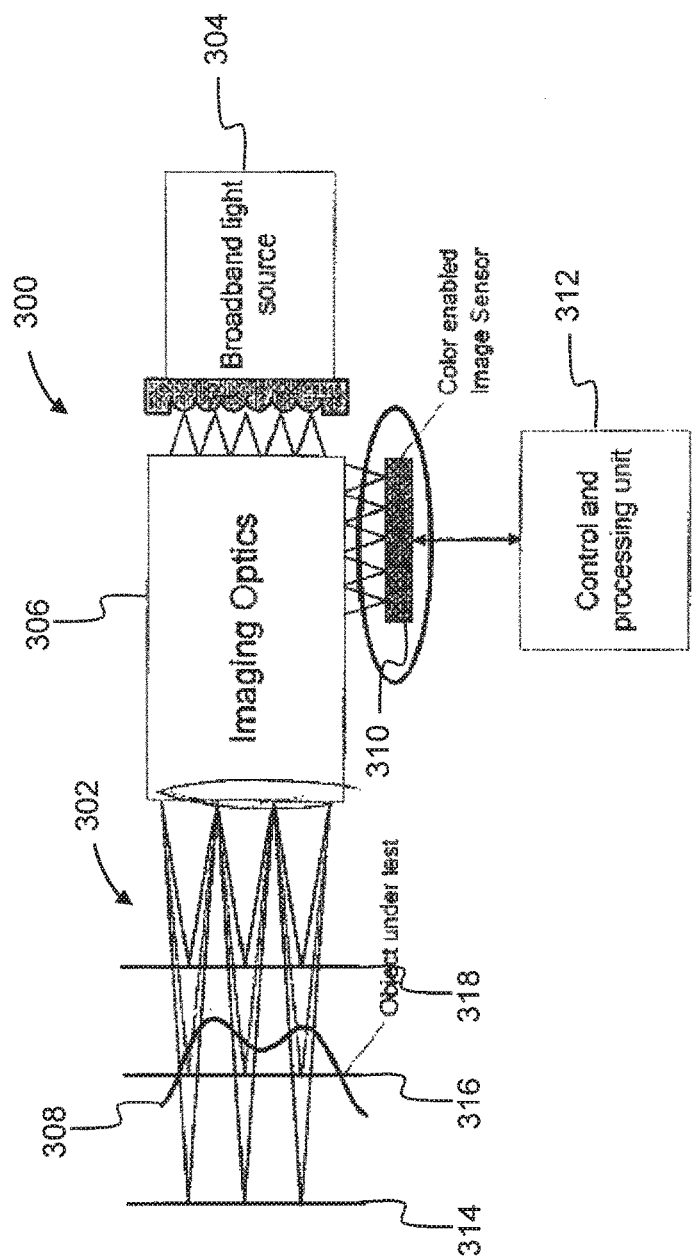
FIG. 4 illustrates an optical system for determining surface topography of a three-dimensional structure, in accordance with many embodiments.

FIG. 4 illustrates an optical system 300 for determining surface topography of a three-dimensional structure, in accordance with many embodiments. The optical system 300 can be combined with any suitable optical measurement system or device, such as the embodiments described herein. In the optical system 300, a two-dimensional array of light beams 302 (e.g., broad-band light beams) emanate from a light source 304. Each of the light beams 302 can include a plurality of wavelengths and can be focused to a corresponding plurality of focal lengths by imaging optics 306. The array of light beams 302 can simultaneously illuminate a three-dimensional structure 308. Light beams reflected from the structure 308 can be transmitted back through the imaging optics 306 and can be diverted by means of a beam splitter (not shown) to a sensor array 310 for measuring intensity (or other characteristic) of different wavelengths. The intensity data is conveyed to a control and processing unit 312 for determination of surface topography based on the measured intensity of the returning wavelengths.

In many embodiments, the light source 304 produces the plurality of light beams 302. The plurality of light beams can be produced by a micro lens array, grating, or other device capable of producing a two-dimensional array. The light source 304 can be a polychromatic or broad-band light source, such that each of the plurality of light beams includes a plurality of different wavelengths, such as a continuous distribution of wavelengths over the visible wavelength spectrum. For example, the light source 304 can include a white light source. Alternatively or in combination, the light source 304 can include a plurality of different monochromatic light sources, such as a red light source, a green light source, and a blue light source.

The imaging optics 306 can include an optical assembly configured to focus each of the light beams 302 to a plurality of focal lengths relative to the optical system 300 or a component of the optical system 300 (e.g., a hand held probe such as the probing member 90). For example, in the embodiment depicted in FIG. 4, representative wavelengths of the light beams 302 are focused to respective representative focal planes 314, 316, and 318. In many embodiments, the light beams 302 include a continuous spectrum of wavelengths focused over a continuous spectrum or range of fixed focal lengths. In many embodiments, the plurality of wavelengths of the light is focused to the plurality of focal lengths without using movable optical components (e.g., using static focusing optics). Any suitable optical component or combination of optical components can be used to focus the wavelengths. For example, the optical assembly can include an optical component (e.g., a lens) with a suitable amount of longitudinal chromatic aberration.

In many embodiments, the optical system 300 can be used to illuminate the structure 308 with the two-dimensional array of light beams so as to form a two-dimensional array of light spots on the structure over a two-dimensional field of view, each light spot having a plurality of wavelengths focused to a corresponding plurality of focal lengths. The geometry and arrangement of the two-dimensional array of spots (e.g., spot size or diameter, pitch or distance between neighboring spots, spot density, etc.) can be configured to reduce noise and increase measurement accuracy of the optical system 300. For example, the ratio of pitch to spot size for the two-dimensional spot array can be selected to minimize or inhibit cross-talk between the spots of the two-dimensional array The use of a two-dimensional array of light spots can provide coverage of the structure 308 over an area lateral to the direction of propagation of the wavelengths, while the focusing of the plurality of wavelengths to a plurality of focal lengths can provide coverage over a distance along the direction of propagation of the wavelengths. Consequently, the three-dimensional surface topography data of the structure can be determined independently of any axial scanning mechanisms or lateral scanning mechanisms used to scan the wavelengths along axial or lateral directions, respectively. For example, the wavelengths can be focused to the appropriate focal depths without movement of any components of the imaging optics 306 relative to any components of the light source 304. Therefore, the imaging optics 306 can be entirely static, without any movable components.

Figure 5:
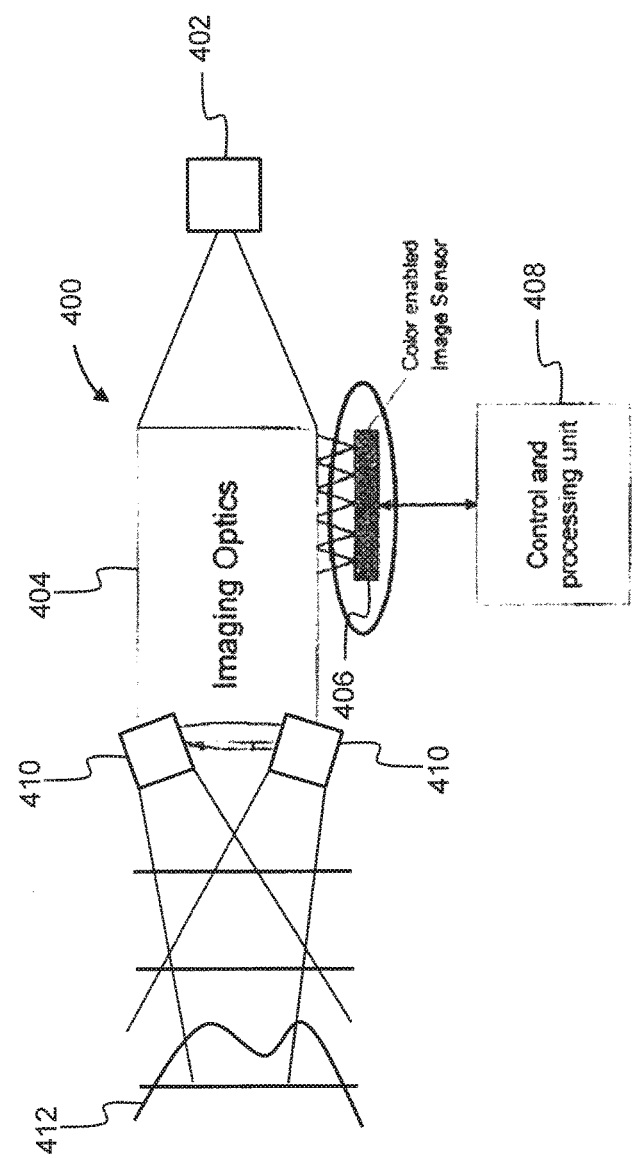
FIG. 5 illustrates another example of an optical system for determining surface topography of a three-dimensional structure, in accordance with many embodiments.

FIG. 5 illustrates another example of an optical system 400, in accordance with many embodiments. Similar to the optical system 300, the optical system 400 includes a light source 402, imaging optics 404, sensor array 406, and control and processing unit 408. However, the optical system 400 provides homogenous or flooding illumination of the structure 412. The flooding illumination may have a plurality of wavelengths, such as a broad-band spectrum of wavelengths. For example, the light source 402 can be an area light source for providing homogenous broad-band spectrum illumination. Alternatively or in combination, the optical system 400 can include a front-end light source 410 providing illumination with a plurality of wavelengths. The front-end light source 410 can be situated at the front end of the optical system 400, near the structure 412 at a position distal to the imaging optics 404. Although the front-end light source 410 is depicted in FIG. 5 as two separate light sources disposed near the imaging optics 404, any suitable configuration of the front-end light source 410 can be used. For example, the front-end light source 410 can be a single light source or a plurality of light sources. The front-end light source 410 can be arranged in any suitable geometry, such as a ring of light sources disposed around the imaging optics 404. In many embodiments, one or more of the light source 402 and front-end light source 410 provides light having a plurality of different wavelengths (e.g., via a polychromatic light source or a plurality of monochromatic light sources as described herein), thereby providing broad-band flooding illumination of the structure 412. Each of the different wavelengths can be focused to a respective different fixed focal length relative to the optical system 400. Accordingly, returning reflections of the light can be directed by the imaging optics 404 to be incident upon the sensor array 406, which measures the relative intensities of the multi-wavelength light. Alternatively or in combination, when the front-end light source 410 is a broad-band or polychromatic light source, the illumination provided by the front-end light 410 source can be not focused, such that the structure 412 is illuminated with all wavelengths equally at all positions relative to the optical system 400. In such embodiments, suitable collecting optics (e.g., chromatic collecting optics included in the imaging optics 404) can be used to focus the returning light beams to different fixed focal lengths incident upon the sensor array 406, which measures the returning light intensities. The sensor array 406 can be operatively coupled to the processing unit 408, which processes the measured intensities to determine surface topography of the structure 412 as described herein. Advantageously, the homogenous illumination optics of the system 400 can be simpler relative to other types of illumination optics. Furthermore, similar to the other optical systems described herein, the system 400 can provide axial and lateral coverage of the structure 412 independently of any axial scanning mechanisms or lateral scanning mechanisms, thereby enabling the imaging optics 404 to operate without using any movable optical components for focusing and scanning the wavelengths of light.

Figure 6B:
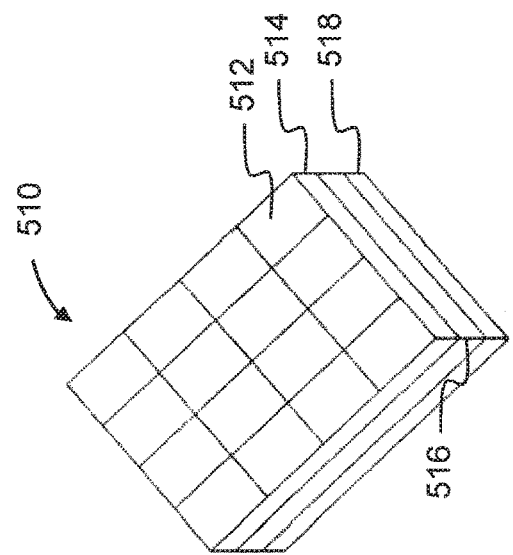
FIG. 6B illustrates another example of a sensor array for measuring intensity of returning wavelengths, in accordance with many embodiments.
Figure 6A:
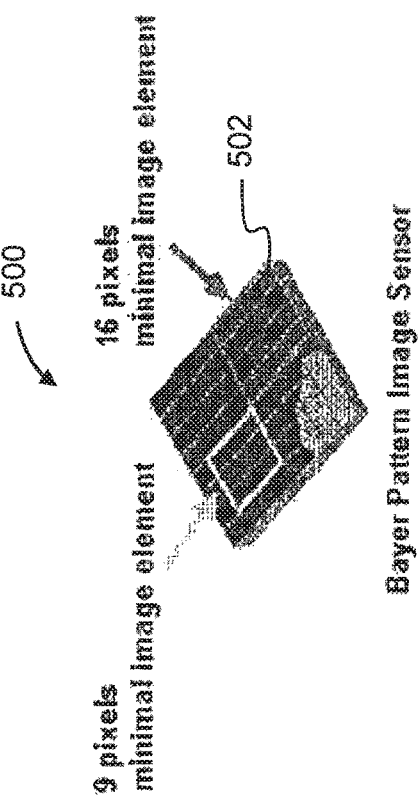
FIG. 6A illustrates a sensor array for measuring intensity of returning wavelengths, in accordance with many embodiments.

FIG. 6A illustrates a sensor array 500, in accordance with many embodiments. The sensor array 500 (e.g., a color detector) can be combined with any of the optical measurement systems and devices described herein. The sensor array 500 includes a plurality of sensor elements 502 (e.g., pixel sensors) arranged in a two-dimensional plane. In many embodiments, the sensor array 500 includes a plurality of different types of sensor elements 502 and each type is configured to measure the intensity of a wavelength component of light. For example, the sensor array 500 can include red sensor elements configured to measure the intensity of a red light wavelength, green sensor elements configured to measure the intensity of a green light wavelength, and blue sensor elements configured to measure the intensity of a blue light wavelength. Other types of sensor elements configured to measure wavelengths other than red, green, or blue can also be used. The sensor array 500 can include any suitable number of different types of sensor elements for measuring any suitable number of different wavelengths. In many embodiments, the wavelengths detected by the sensor elements 502 correspond to the wavelengths focused to different fixed focal lengths by a suitable optical assembly, as described herein.

The sensor array 500 can include any suitable number of the sensor elements 502. For example, the number of red sensor elements, green sensor elements, and blue sensor elements present in the sensor array 500 can be equal. Conversely, one or more types of sensor elements can be more numerous than one or more other types of sensor elements. The different types of sensor elements can be arranged in any suitable pattern, such as a Bayer pattern or modified Bayer pattern. Other sensor array patterns suitable for use with the sensor arrays described herein include RGBE patterns, CYYM patterns, CYGM patterns, RGBW Bayer patterns, RGBW #1 patterns, RGBW #2 patterns, RGBW #3 patterns, and so on. A minimal image element of the sensor array 500 can include any suitable number of sensor elements. For example, as depicted in FIG. 6A, the minimal image element can include nine sensor elements or sixteen sensor elements. In many embodiments, a minimal image element includes at least one of each sensor element type, such that the intensity data from the minimal image element includes intensity data from all of the wavelengths. In many embodiments, the optical assembly is configured such that each returning reflected light beam is directed to be incident on a respective one of the minimal image elements of the sensor array 500.

FIG. 6B illustrates another example of a sensor array 510, in accordance with many embodiments. The sensor array 510 can be combined with any of the optical measurement systems and devices described herein. The sensor array includes a plurality of sensor elements 512 arranged in a plurality of layers, such as a first layer 514, a second layer 516, and a third layer 518. The layers 514, 516, and 518 can be fabricated from any suitable material that is transmissive to at least some wavelengths of light (e.g., silicon). The penetration depth of light in the layers 514, 516, and 518 can depend on the wavelength of the light. For example, a red wavelength can have a greater penetration depth than a green wavelength, which can have a greater penetration depth than a blue wavelength.

The sensor elements 512 can include a plurality of different types of sensor elements, each configured to measure the intensities of a different wavelength of light as previously described. In many embodiments, each of the layers 514, 516, 518 includes a single type of sensor element. For example, the first layer 514 can include only blue sensor elements, the second layer 516 can include only green sensor elements, and the third layer 518 can include only red sensor elements. Alternatively, some of the layers can include sensor elements of more than one type. The positioning of a sensor element type within the different layers can be based on the penetration depth of the corresponding measured wavelength. In many embodiments, sensor elements corresponding to wavelengths with greater penetration depths are situated farther from the incident light, and sensor elements corresponding to wavelengths with smaller penetration depths are situated closer to the incident light. In many embodiments, a minimal image element of the sensor array 510 includes a single sensor from each layer, the sensors being positioned vertically adjacent to each other. Accordingly, the size (e.g., horizontal surface area) of a minimal image element of the sensor array 510 can be the same as the size (e.g., horizontal surface area) of a single sensor element.

Figure 7:
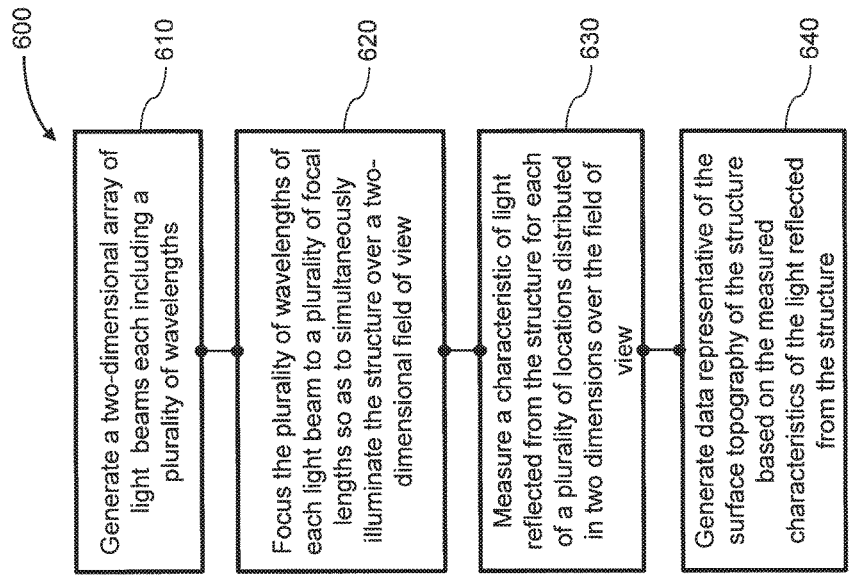
FIG. 7 is a schematic illustration by way of block diagram of a method for determining surface topography of a three-dimensional structure, in accordance with many embodiments.

FIG. 7 is a schematic illustration by way of block diagram of a method 600 for determining surface topography of a three-dimensional structure, in accordance with many embodiments. Any suitable device or system can be used to practice the method 600, such as the embodiments described herein.

In step 610, a two-dimensional array of light beams is generated. The array can be generated using a suitable illumination unit and optics (e.g., microlens array), as previously described herein. Each light beam can include a plurality of wavelengths. The plurality of wavelengths can be discrete wavelengths or a continuous spectrum of wavelengths.

In step 620, the plurality of wavelengths of each light beam is focused to a plurality of focal lengths relative to the structure so as to illuminate the structure over a two-dimensional field of view. The two-dimensional array of light beams may be projected onto the structure so as to form a two-dimensional array of light spots. The plurality of wavelengths of each light beam can be focused using a suitable optical assembly or other imaging optics, as described elsewhere herein. The plurality of focal lengths may be a plurality of discrete focal lengths or a continuous spectrum of focal lengths. In many embodiments, the focusing is performed without using movable optical components, thus obviating the need for axial scanning mechanisms or movement of focusing optics relative to an illumination source, as previously described herein. Furthermore, the structure can be illuminated with area illumination or an array of light beams, such that no movable optical components are needed to scan the wavelengths axially or laterally.

In step 630, a characteristic of the light reflected from the structure is measured for each of a plurality of locations distributed in two dimensions over the field of view. The reflected light may include a plurality of wavelengths corresponding to the wavelengths of the incident light. In many embodiments, the characteristic is intensity, although other characteristics can also be used, as described elsewhere herein. A suitable sensor array or color detector can be used to measure the intensities, as previously described herein. In many embodiments, the sensor is a two-dimensional or area sensor. For example, the sensor can be a Bayer patterned color detector, a multilayered color detector (e.g., a FOVEON X3® sensor), or any other color detector having a suitable sensor array pattern, as previously described herein.

In step 640, data representative of the surface topography of the three-dimensional structure is generated, based on the measured characteristics of the light reflected from the structure. For example, in many embodiments, the returning wavelength having the highest measured intensity corresponds to an incident wavelength focused on the surface of the structure. Accordingly, the fixed focal length of the incident wavelength can be used to determine the relative height of the point on the structure. By determining the intensities of light returning from a plurality of locations on the structure, the overall three-dimensional surface topography can be reconstructed.

Although the above steps show method 600 of determining surface topography in accordance with many embodiments, a person of ordinary skill in the art will recognize many variations based on the teaching described herein. Some of the steps may comprise sub-steps. Many of the steps may be repeated as often as appropriate. One or more steps of the method 600 may be performed with any suitable system, such as the embodiments described herein. Some of the steps may be optional. For example, step 620 may be optional, such that the light may not be focused prior to illuminating the structure, as previously described with respect to the embodiments providing front-end homogeneous illumination.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for measuring surface topography of a three-dimensional structure, the system comprising:
    an illumination unit configured to output an array of light beams, each light beam comprising a plurality of wavelengths;
    an optical assembly configured to receive the array of light beams from the illumination unit and to focus the plurality of wavelengths of each light beam to a plurality of fixed focal lengths so as to illuminate the three-dimensional structure over a field of view; and
    a detector configured to measure a characteristic of light reflected from the three-dimensional structure for each of a plurality of locations in the field of view,
    wherein the array of light beams form spots on the three-dimensional structure over the field of view, and wherein a ratio of pitch to spot size for the spots is configured to inhibit cross-talk between the spots.

2. The system of claim 1, wherein the characteristic comprises an intensity of the light reflected from the three-dimensional structure.

3. The system of claim 2, wherein the detector comprises a plurality of sensor elements distributed over a surface area configured to receive the light reflected from the three-dimensional structure over the field of view.

4. The system of claim 3, wherein each sensor element of the plurality of sensor elements is configured to measure the intensity of at least one wavelength of the light reflected from the three-dimensional structure.

5. The system of claim 1, wherein the plurality of wavelengths comprises wavelengths from 400 nm to 800 nm.

6. The system of claim 1, wherein the plurality of wavelengths comprises at least three spectral bands, and wherein the at least three spectral bands comprise overlapping wavelengths of light.

7. The system of claim 1, wherein the plurality of wavelengths comprises a continuous spectrum of wavelengths.

8. The system of claim 1, wherein the optical assembly is configured to focus the light beams to the plurality of focal lengths using at least one optical component with longitudinal chromatic aberration.

9. The system of claim 1, wherein the plurality of focal lengths covers a depth of at least 20 mm.

10. The system of claim 1, wherein the optical assembly is configured to focus the plurality of wavelengths to the plurality of focal lengths to a depth within a range from 10 mm to 30 mm relative to the optical assembly without relative movement of components of the optical assembly and components of the illumination unit.

11. A system for measuring surface topography of a three-dimensional structure, the system comprising:
    an illumination unit configured to output an array of light beams, each light beam comprising a plurality of wavelengths;
    an optical assembly configured to receive the array of light beams from the illumination unit and to focus the plurality of wavelengths of each light beam to a plurality of fixed focal lengths so as to illuminate the three-dimensional structure over a field of view; and
    a detector configured to measure a characteristic of light reflected from the three-dimensional structure for each of a plurality of locations in the field of view, wherein the characteristic comprises an intensity of the light reflected from the three-dimensional structure, the detector comprises a plurality of sensor elements distributed over a surface area configured to receive the light reflected from the three-dimensional structure over the field of view, each sensor element of the plurality of sensor elements is configured to measure the intensity of at least one wavelength of the light reflected from the three-dimensional structure, and the plurality of sensor elements comprises a plurality of red sensor elements, a plurality of green sensor elements, and a plurality of blue sensor elements, each of the plurality of red sensor elements being configured to measure the intensity of a red light wavelength, each of the plurality of green sensor elements being configured to measure the intensity of a green light wavelength, and each of the plurality of blue sensor elements being configured to measure the intensity of a blue light wavelength.

12. The system of claim 11, wherein the plurality of sensor elements are arranged in a Bayer pattern or in a plurality of layers.

13. A method for measuring surface topography of a three-dimensional structure, the method comprising:
    generating an array of light beams, each light beam comprising a plurality of wavelengths;
    projecting each light beam onto the three-dimensional structure over a field of view, the plurality of wavelengths of each light beam being projected at a respective plurality of fixed focal lengths relative to an optical assembly;
    measuring a characteristic of light reflected from the three-dimensional structure for each of a plurality of locations; and
    outputting the measured characteristic of light,
    wherein the array of light beams forms spots on the structure over the field of view, and wherein a ratio of pitch to spot size for the spots is selected to inhibit cross-talk between the spots.

14. The method of claim 13, wherein the characteristic comprises an intensity of the light reflected from the three-dimensional structure.

15. The method of claim 14, wherein the intensity of the light reflected from the three-dimensional structure is measured using a detector comprising a plurality of sensor elements distributed over a surface area configured to receive the light reflected from the three-dimensional structure over the field of view.

16. The method of claim 15, wherein each sensor element of the plurality of sensor elements is configured to measure the intensity of at least one wavelength of the light reflected from the three-dimensional structure.

17. The method of claim 13, wherein the plurality of wavelengths comprises wavelengths from 400 nm to 800 nm.

18. The method of claim 13, wherein the plurality of wavelengths comprises at least three spectral bands, and wherein the at least three spectral bands comprise overlapping wavelengths of light.

19. The method of claim 13, wherein the plurality of wavelengths comprises a continuous spectrum of wavelengths.

20. The method of claim 13, wherein the light beams are focused to the plurality of focal lengths using at least one optical component with longitudinal chromatic aberration.

21. The method of claim 13, wherein the plurality of focal lengths covers a depth of at least 20 mm.

22. The method of claim 13, further comprising focusing of the plurality of wavelengths to the plurality of focal lengths to a depth within a range from 10 mm to 30 mm is performed without relative movement of components of an optical assembly and components of an illumination unit.

23. A method for measuring surface topography of a three-dimensional structure, the method comprising:
    generating an array of light beams, each light beam comprising a plurality of wavelengths;
    projecting each light beam onto the three-dimensional structure over a field of view, the plurality of wavelengths of each light beam being projected at a respective plurality of fixed focal lengths relative to an optical assembly;
    measuring a characteristic of light reflected from the three-dimensional structure for each of a plurality of locations, wherein the characteristic comprises an intensity of the light reflected from the three-dimensional structure, wherein the intensity of the light reflected from the three-dimensional structure is measured using a detector comprising a plurality of sensor elements distributed over a surface area configured to receive the light reflected from the three-dimensional structure over the field of view, each sensor element of the plurality of sensor elements is configured to measure the intensity of at least one wavelength of the light reflected from the three-dimensional structure and wherein the plurality of sensor elements comprises a plurality of red sensor elements, a plurality of green sensor elements, and a plurality of blue sensor elements, each of the plurality of red sensor elements being configured to measure the intensity of a red light wavelength, each of the plurality of green sensor elements being configured to measure the intensity of a green light wavelength, and each of the plurality of blue sensor elements being configured to measure the intensity of a blue light wavelength; and
    outputting the measured characteristic of light.

24. The method of claim 23, wherein the plurality of sensor elements are arranged in a Bayer pattern or in a plurality of layers.

* * * * *